United States Patent [19]

Hannart

[11] 4,285,949
[45] Aug. 25, 1981

[54] VINCAMINE DERIVATIVES, THEIR PREPARATION AND THERAPEUTICAL USE

[75] Inventor: Jean A. A. J. Hannart, Chaumont-Gistoux, Belgium

[73] Assignee: Omnichem Societe Anonyme, Brussels, Belgium

[21] Appl. No.: 968,147

[22] Filed: Dec. 11, 1978

[51] Int. Cl.³ .................. A61K 31/445; C07D 461/00
[52] U.S. Cl. ....................................... 424/256; 546/51
[58] Field of Search ......................... 546/51; 424/256

[56] References Cited

U.S. PATENT DOCUMENTS

| | | | |
|---|---|---|---|
| 3,799,933 | 3/1974 | Le Men et al. | 546/51 |
| 3,892,755 | 7/1975 | Levy | 546/51 |
| 3,894,028 | 7/1975 | Levy | 546/51 |
| 3,979,395 | 9/1976 | Taccone | 546/51 |
| 4,033,969 | 7/1977 | Sevenet et al. | 546/51 |
| 4,140,777 | 2/1979 | Vegezzi | 546/51 |
| 4,145,552 | 3/1979 | Heymés | 546/51 |
| 4,146,643 | 3/1979 | Pfäffli | 424/262 |

FOREIGN PATENT DOCUMENTS

| | | |
|---|---|---|
| 2458164 | 6/1975 | Fed. Rep. of Germany . |
| 2800063 | 7/1979 | Fed. Rep. of Germany ........... 424/256 |
| 2092726 | 1/1972 | France .................... 424/256 |
| 2359147 | 2/1978 | France . |

OTHER PUBLICATIONS

Subject Index (1967-1971) of Chemical Abstracts, subj., Vincamine, p. 328075.

Primary Examiner—Donald G. Daus
Assistant Examiner—Diana G. Rivers
Attorney, Agent, or Firm—Pollock, Vande Sande & Priddy

[57] ABSTRACT

The new derivatives of vincamine according to this invention may be represented by the general formula

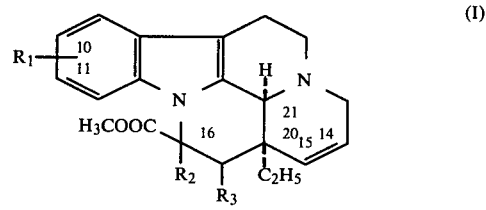

in which $R_1$ represents a halogen atom and $R_2$ may represent a hydroxy group whereas $R_3$ may represent a hydrogen atom, or $R_2$ may form with $R_3$ an additional bond.

The compounds may be used to treat cardio-circulatory, cerebro-vascular and respiratory insufficiencies.

5 Claims, No Drawings

VINCAMINE DERIVATIVES, THEIR PREPARATION AND THERAPEUTICAL USE

The present invention relates to new heterocyclic compounds, their preparations and therapeutical use as active drug ingredients.

More particularly the invention relates to heterocyclic compounds of the formula

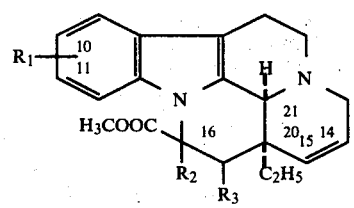

in which:

$R_1$ represents a halogen atom in the 10- or 11-position;
$R_2$ represents a hydroxy group and $R_3$ represents a hydrogen atom;
or $R_1$ represents a halogen atom in the 10- or 11-position and $R_2$ and $R_3$ form together and additional bond between the two carbon atoms which carry them, and the salts formed by said compounds with inorganic or organic acids.

The compounds of formula I may exist as optical isomers (16, 20, 21) and racemic mixtures.

All of these forms pertain of course to this invention.

The invention also has for its object a process for preparing said new derivatives of vincamine which comprises reacting a halohydrate or hydrohalide of tabersonine in solution in an alcohol for 2 to 4 days at room temperature in the presence of a peracid such as m.chloroperbenzoic acid, perphthalic acid and p.nitroperbenzoic acid.

The derivative I, in which $R_1$ represents a halogen atom and $R_2$ and $R_3$ form together an additional bond between the two carbon atoms to which they are attached, is obtained in conventional way by dehydrating in acid medium the corresponding derivative I wherein $R_1$ represents a halogen atom, $R_2$ represents a hydroxy group and $R_3$ represents a hydrogen atom.

The following examples describe in non limitative way the features of the invention.

EXAMPLE 1. 10-Chloro-16-epiΔ14-vincamine ($R_1$=10-Cl; $R_2$=OH, $R_3$=H) (OC-231 E)

1 g of tabersonine is dissolved in 50 ml of methanol. To the solution thus obtained, one adds successively 30 ml of 1/10 N hydrochloric acid and then 0.006 M of metachloroperbenzoic acid. The reaction mixture is then stirred for 60 hours at room temperature.

The reaction mixture is flooded with water, made alkaline by means of potassium carbonate and extracted with chloroform.

After it has been washed, dried and evaporated to dryness, the chloroform phase gives 1.3 of dry residue.

The product I crystallises from methanol or acetone. m.p.: 196°–198° C.

$(\alpha)_D$= +91.5° (c=1, CHCl$_3$)

I.R. Spectrum (KBr): bands at 3440, 3040, 2980–2880, 1735, 1590, 1460–1440 cm$^{-1}$ U.V. Spectrum (MeOH) λnm (log.ε): 232 (4.41); 282 (3.76); 289 (3.75); 300 (3.58).

N.M.R. Spectrum (CDCl$_3$) δ(ppm): 0.9 (t, 3H); 2.05 (d, 1H); 2.66 (d, 1H); 3 (m, 3H); 3.25 (m, 2H); 3.46 (s, 3H); 3.76 (s, 1H); 5.3 (m, 1H); 5.52 (d, 1H); 7.06 (m, 1H); 7.33 to 7.63 (m, 2H).

Mass spectrum: M+ calculated for $C_{21}H_{23}N_2O_3Cl$=386; found=386

Analysis: calculated for $C_{21}H_{23}N_2O_3Cl$

|  | % C | % H | % N |
| --- | --- | --- | --- |
| Calculated | 65.17 | 5.97 | 7.24 |
| Found | 65.06 | 6.01 | 7.34 |

EXAMPLE 2. 10-Chloro-Δ14-vincamine ($R_1$=10-Cl; $R_2$=OH, $R_3$=H) (OC-231 N)

1 g of 10-chloro-16-epi-Δ14-vincamine is dissolved in 50 ml of methanol at 5% of potassium hydroxide. The solution thus obtained is stirred 24 hours at room temperature.

The reaction mixture is flooded with water and extracted with chloroform. Said chloroform having been washed, dried and evaporated to dryness, gives 1 g of dry product.

The product crystallises from methanol. m.p.: 194° C.

$(\alpha)_D$= +160° (c=1, MeOH)

I.R. Spectrum: (CHCl$_3$): bands at 3500 2960–2820, 1750, 1640, 1600, 1460–1445 cm$^{-1}$ U.V. Spectrum (CH$_3$OH)λnm (log.ε): 233.5 (4.41); 282 (3.86); 289 (3.88); 299 (3.77)

N.M.R. Spectrum (CDCl$_3$)δ(ppm): 0.99 (t, 3H); 1.4–2.1(m,2H); 2.33 (s, 2H); 3.06 (m,2H); 3.55 (m, 2H); 3.86 (s,3H); 3.88 (s, 3H); 4.1 (s, 1H); 5.73 (m, 2H); 7.06 (m, 2H); 7.5 (m, 1H).

Mass Spectrum: M+calculated doe $C_{21}H_{23}N_2O_3Cl$:386; found: 386

Analysis: calculated for $C_{21}H_{23}N_2O_3Cl$

|  | % C | % H | % N |
| --- | --- | --- | --- |
| Calculated | 65.17 | 5.97 | 7.24 |
| found | 65.14 | 5.89 | 7.21 |

EXAMPLE 3.: 10-Chloro-apo-Δ14-vincamine ($R_1$=10-Cl; $R_2$ and $R_3$=additional bond (OC-233)

1 g of the product described in example 1 or in example 2, having been dissolved in 100 ml of formic acid at 99% is heated four hours at reflux.

After it has been flooded with water, made alkaline with potassium carbonate, extracted with chloroform, the reaction mixture gives 0.9 g of dry extract. The product crystallises from methanol. m.p.: 160° C.

$(\alpha)_D$=145.5° (c=1, CHCl$_3$)

I.R. Spectrum (CHCl$_3$): bands at 2940–2820, 1735, 1635, 1615, 1450, 1280, 1100, 990, 950 cm$^{-1}$ U.V. Spectrum (CH$_3$OH)λnm (log.ε): 234 (4.5); 279 (4.12); 322 (3.92).

N.M.R. Spectrum (CDCl$_3$)δ(ppm): 1.15 (t,3H); 1.86 (m,2H); 2.46 (m,1H); 3.13 (m,3H); 3.4 (m,2H); 4.03 (s,3H); 4.3 (s,1H); 5.5 (m,2H); 6.17 (s,1H); 7.13 (m,2H); 7.5 (m,1H).

Mass spectrum: M+ calculated for $C_{21}H_{21}N_2O_2Cl$=368; found: 368

Analysis: calculated for $C_{21}H_{21}N_2O_2Cl$

|  | % C | % H | % N |
|---|---|---|---|
| Calculated | 68.38 | 5.73 | 7.59 |
| Found | 68.31 | 5.76 | 7.51 |

The invention also comprises the industrial and among others pharmaceutical uses of the products described hereabove. Indeed, the main compounds of formula I have been subjected to pharmacological tests which have shown interesting properties. Vincamine has been selected as the control substance.

ACUTE TOXICITY

The compounds of the invention as well as vincamine were administered by intravenous route to Charles River stock mice. The 50% lethal doses ($LD_{50}$) where determined graphically according to the method of Lichtfield and Wilcoxon (J. Pharmacol. Exp. Therap. 1946, 96, 99).

The results are summarized in Table I.

TABLE I

| Compound | $LD_{50}$ mg/kg i.v. |
|---|---|
| Vincamine | 47 |
| OC-231 E | 47 |
| OC-231 N | 47 |
| OC-233 | 52 |

The compounds of the invention have a toxicity comparable with that of vincamine.

HYPOBARIC ANOXIA TEST ON MICE.

Charles River stock mice of the same sex, weighing about 20±2 g are shared into three lots of 10 animals each. The lots 1 and 2 comprise treated animals, i.e. those having received either a substance to be tested or vincamine, together with solvent, at 1 ml/100 g of body weight. The third lot comprises control animals i.e. those having only received solvent at 1 ml/100 g of body weight.

The compounds examined are administered by intragastric route 15 minutes before the experiment.

The animals are placed in an atmosphere impoverished in oxygen by creating a partial vacuum (190 mm Hg, corresponding to 5.25% oxygen), in about 30 seconds.

The survival time of the mice is measured with a chronometer. Said time is increased by the agents capable of enhancing oxygenation of tissues and more particularly brain oxygenation. The percentages of survival time increase with respect to the values obtained for the control animals are calculated.

The effects obtained with the compounds of formula I compared with vincamine are summarized in table II.

The doses were selected to obtain a 50-70% increase of the survival time of the animals under the experimental conditions.

Generally speaking, the products of the invention all have an anti-anoxic activity which appears at smaller doses than the active doses of vincamine.

TABLE II

| Lot | Survival time | Variation % | Doses mg/kg |
|---|---|---|---|
| Control | 39 (±2) | | |
| Vincamine | 58 (±4) | +49% | 200 |
| OC-231 E | 62 (±6) | +55% | 30 |
| OC-233 | 57 (±4) | +46% | 20 |
| OC-231 N | 60 (±1) | +53% | 30 |

These pharmaceutical properties cause the compounds of formula I to be therapeutically valuable in human and veterinary medicine, among others against cardio-circulatory, cerebro-vascular and respiratory insufficiencies.

For their therapeutical uses, the compounds of formula I may be administered either by digestive route in the form of capsules, tablets, pellets, dragees, cachets, solutions or suspensions or by parenteral route as buffered sterile solutions, prepared beforehand or extemporaneously, in which the active substance, base or salt, is present in an amount of 1 mg to 200 mg per unit. The daily dose may vary between 3 mg and 600 mg according to the disease.

It should be understood that many changes may be brought by the skilled art man to the process and products described hereinabove only as non-limiting examples and still remain within scope of this invention.

What I claim is:

1. A process for preparing a compound of the formula

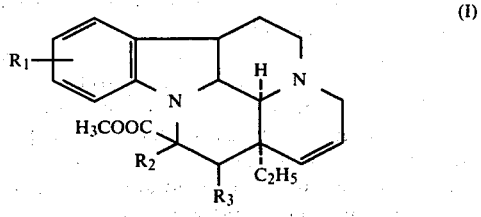

(I)

in which:
R₁ represents a chlorine atom in the 10-position
R₂ and R₃ represent together an additional carbon-carbon bond which comprises the steps of:
(a) reacting tabersonine with hydrochloric acid in solution in an alcohol for 2-4 days at room temperature in the presence of a peracid selected from the group consisting of m-chloroperbenzoic acid, perphthalic acid and p-nitroperbenzoic acid,
(b) heating the resulting compound of formula I wherein R₂ and R₃ represent respectively OH and H in formic acid at 99%.

2. A process according to claim 1 in which the heating of step (b) is effected at reflux for four hours.

3. A compound of formula I as defined in claim 1 being 10-chloro dehydro-14,15 apovincamine (or 10-chloro $\Delta_{14,15}$ apovincamine).

4. A pharmaceutical composition for use in human and veterinary medicine in treating cardio circulatory, cerebrovascular and respiratory insufficiencies, containing an effective amount of about 1 to 200 mg of an active ingredient comprising at least the compound of formula I as defined in claim 1 together with a pharmaceutically acceptable carrier.

5. A method of treating cardiocirculatory, cerebrovascular and respiratory insufficiency comprising daily administration to a patient in need of such treatment of a pharmaceutical composition comprising 3 mg to 600 mg daily dosage of the vincamine derivative as defined in claim 1 in its base or salt form together with a pharmaceutically acceptable excipient.

* * * * *